US011644405B2

(12) United States Patent
Zhang et al.

(10) Patent No.: US 11,644,405 B2
(45) Date of Patent: May 9, 2023

(54) USE OF TUMOR DISSOCIATION REAGENT IN FLOW CYTOMETRY

(71) Applicant: WuXi AppTec (Suzhou) Co. Ltd., Suzhou (CN)

(72) Inventors: Ning Zhang, Suzhou (CN); Qiyao Zhang, Suzhou (CN); Yan Liu, Suzhou (CN); Qunsheng Ji, Suzhou (CN)

(73) Assignee: WuXi AppTec (Suzhou) Co. Ltd., Suzhou (CN)

( * ) Notice: Subject to any disclaimer, the term of this patent is extended or adjusted under 35 U.S.C. 154(b) by 140 days.

(21) Appl. No.: 16/570,083

(22) Filed: Sep. 13, 2019

(65) Prior Publication Data

US 2020/0116622 A1 Apr. 16, 2020

Related U.S. Application Data

(62) Division of application No. 15/486,562, filed on Apr. 13, 2017, now abandoned.

(30) Foreign Application Priority Data

Apr. 15, 2016 (CN) .......................... 201610235031.4

(51) Int. Cl.
| | |
|---|---|
| *G01N 15/14* | (2006.01) |
| *G01N 33/574* | (2006.01) |
| *G01N 33/569* | (2006.01) |
| *G01N 33/535* | (2006.01) |
| *G01N 33/483* | (2006.01) |
| *G01N 15/10* | (2006.01) |
| *G01N 1/40* | (2006.01) |
| *G01N 15/00* | (2006.01) |
| *G01N 33/48* | (2006.01) |

(52) U.S. Cl.
CPC .......... *G01N 15/14* (2013.01); *G01N 33/483* (2013.01); *G01N 33/535* (2013.01); *G01N 33/56966* (2013.01); *G01N 33/574* (2013.01); *G01N 33/57484* (2013.01); *G01N 1/4044* (2013.01); *G01N 15/00* (2013.01); *G01N 15/1459* (2013.01); *G01N 33/48* (2013.01); *G01N 2015/1006* (2013.01)

(58) Field of Classification Search
CPC .......... G01N 33/535; G01N 33/56966; G01N 33/57484; G01N 1/4044; G01N 15/14
See application file for complete search history.

(56) References Cited

U.S. PATENT DOCUMENTS

2003/0129206 A1 7/2003 Ulbrich et al.
2007/0148666 A1 6/2007 Vibhakar et al.

FOREIGN PATENT DOCUMENTS

CN 107988118 A 10/2015
WO 2006/030473 A1 3/2006

OTHER PUBLICATIONS

Punjaruk et al., Different Enzyme Cocktail Conditions Successfully Establish Primary Brain Tumor Cell Line Derived from Pilomyxoid Astrocytoma Patient, Srinagarind Med J, 2015; 30(2): 137-148.*
Hartfuss et al., Characterization of CNS Precursor Subtypes and Radial Glia, Developmental Biology, 2001, 229:15-30.*
Joannes et al. Regulatory T cells and the PD-L1/PD-1 pathway mediate immune suppression in malignant human brain tumors, Neuro-Oncology, 2009, 11:394-402.*
Pardoll, The blockade of immune checkpoints iin cancer immunotherapy, Nature Reviews, 2012, 12: 252-264.*
Reichard et al., Cytometry Part A, 2019, 95A: 219-226.*
Product Information of Sigma Cat. No. H3506, available before Apr. 2014.*
Chen et al., Nature, 2014, 508, 13119, 17 pages.*
Kang et al., Research of Hyaluronidases and Future Development, Biotechnollogy Bulletin, 2014, 7 pages.
Hsu et al., Effects of chondroitin sulfate proteoglycan 4 (NG2/CSPG4) on soft tissue sarcoma growth depend on tumor developmental stage, JPC Papers in Press, Dec. 1, 2017, 26 pages.
Hurt-Camejo et al., CD44, a Cell Surface Chondroitin Sulfate Proteoglycan, Mediates Binding of Interferon-g and Some of Its Biological Effects on Human Vascular Smooth Muscle Cells, The Journal of Biological Chemistry, vol. 274, No. 27, Issue of Jul. 2, pp. 18957-18964, 1999.
Stern et al., Hyaluronidase Can Modulate Expression of CD44, Experimental Cell Research 266, 167-176 (2001), 10 pages.
Punjaruk et al., "Different Enzyme Cocktail Conditions Successfully Establish Primary Brain Tumor Cell Line Derived from Pilomyxoid Astrocytoma Patient," Srinagarind Medical Journal, 30 (2): 137-148 (2015).
Hitchcock et al., "Mononuclear cell infiltration in central portions of human astrocytomas," Journal of Neurosurgery, 68: 432-437 (1988).
Saric et al., "Ornithine Decarboxylase in Pneumocystis carinii and Implications for Therapy," Antimicrobial Agents and Chemotherapy, 38 (11): 2545-2552 (1994).
Leadbetter et al., "Chromatin-IgG complexes activate B cells by dual engagement of IgM and Toll-like receptors," Nature, 416: 603-607 (2002).

(Continued)

*Primary Examiner* — Hong Sang
(74) *Attorney, Agent, or Firm* — Procopio, Cory, Hargreaves & Savitch LLP

(57) ABSTRACT

The present disclosure relates to a dissociation reagent for tumor tissues. The dissociation reagent does not contain collagenase or trypsin but further contains hyaluronidase or a mixture of hyaluronidase and DNase I. The present disclosure also relates to use of the dissociation reagent in dispersing tumor tissues and detecting expression level of molecular markers on cell surface by flow cytometry. The dissociation reagent of the present disclosure does not cause degradation of molecular markers on cell surface such as CD8, PD-1, Tim-3, Lag-3 and the like, thus does not affect downstream assays.

3 Claims, 5 Drawing Sheets

(56) References Cited

OTHER PUBLICATIONS

Wang et al., "Effects of hyaluronidase and hyaluronan on proliferation of vascular endothelial cells and the expression of CD44," Academic Journal of Second Military Medical University, 22 (2): 144-147 (2001) (see English abstract).
Saifia et al., "Galanin inhibits glucagon-like peptide-1 secretion through pertussis toxin-sensitive G protein and ATP-dependent potassium channels in rat ileal L-cells," Journal of Endocrinology, 157: 33-41 (1998).
Stratagene Catalog, p. 39 (1988).

* cited by examiner

USE OF TUMOR DISSOCIATION REAGENT IN FLOW CYTOMETRY

CROSS-REFERENCE TO RELATED APPLICATION

This application claims priority to Chinese Application No. 201610235031.4 filed on Apr. 15, 2016, which is incorporated herein by reference in its entirety.

FIELD OF THE INVENTION

The present disclosure relates to a tumor dissociation reagent useful in flow cytometry for dispersing a clinical solid tumor tissue into a single cell suspension and for protecting the surface marker from being degraded.

BACKGROUND

In the analysis of the cell biological characteristics of tumor tissue (such as the detection of cell epitope, etc.), preparation in tissue blocks of the sample into a single cell suspension is required, so as to obtain high-yield cells, and integrity of cells and epitopes is intact and can be used directly in downstream experiments. Only when various cell components of the sample tissue are in a single cell state, a variety of detection and analysis of cell effects can be effectively carried out, while the quality of cell suspension is closely related to digestive fluid formulations and digestion methods. The preparation methods of single cell suspension commonly used are chemical, enzymatic and physical methods.

The cell-to-cell linkages such as collagenase, elastic fiber, mucopolysaccharide, tight junction proteins and the like are mainly destructed for cell dispersion in enzymatic method. Trypsin, collagenase, hyaluronidase and the like are the commonly used enzymes. In prior art, it is stated that a variety of tissues including tumor tissue, skeletal muscle, spleen, lung, nerve tissue, epidermis, lamina propria, mouse heart, neonatal neurons, embryoid bodies and the like may be treated with commercial dissociation kits such as the Miltenyi Tissue Dissociation Kit; and according to the difference in the sensitivity of the cell surface antigen to enzymatic digestion, different enzyme reaction systems are designed for preventing the cell surface antigen destruction, so as not to affect downstream experiments. In fact, there are some molecular markers on cell surface that are degraded or partially degraded in practices, making it impossible to detect accurately.

In fact, some commonly used components of the enzymatic reagent will affect the detection of cell surface molecular markers. For example, Trypsin has a strong ability to disperse cells with short action time. The use of trypsin in preparation of single cell suspension results in high yield, but the conditions of action required by trypsin are complex. In addition, Trypsin may damage the cell surface antigen and even cells. For example, trypsin-treated mouse thymus cell surface receptors CD4 and CD8 are digested by trypsin digestion (Thomas Barthlott, Rebecca J. Wright and Brigitta Stockinger. *J Immunol*, 1998. 161:3992-3999). Therefore, trypsin is suitable for detection of intracellular antigens but not for cell surface antigens, especially weakly expressed antigens.

Immunological checkpoint proteins are key targets in tumor therapy and play a very important role in immunotherapy, thus may be a powerful weapon for conquering cancer. Therefore the accuracy of detection is required for diagnosis and treatment of cancer.

In the process of diagnosis and determination of the following treatment regimen (especially targeted therapy) for clinical cancer patients, flow cytometry has an incomparable advantage in determination of subdivision and cell surface markers, because it can simultaneously detect multiple markers on a single cell. However, the tumor tissue needs to be treated with a digestive enzyme into a single cell suspension before it can be used for subsequent flow cytometry. In the present disclosure, we have found that the current commercial human tumor digestive agents or digestive agents commonly used such as collagenases all have a significant impact on the expression level of various proteins concerned in the present disclosure (including immunological checkpoint proteins such as Tim-3 and Lag3), which undoubtedly increased the risk of misdiagnosis of the disease and easily lead to wrong treatment. Therefore, the digestive effect of dissociation reagent on tumor tissues and the protective effect thereof on cell surface antigen remain to be improved. It is important to find a digestive enzyme or mixture that is effective in digesting human tumor tissues and does not affect the expression of surface markers.

SUMMARY

In one aspect, the present disclosure relates to a tumor dissociation reagent.

Wherein, the tumor dissociation reagent which does not comprise collagenase but comprises hyaluronidase, said tumor dissociation reagent does not degrade or partially degrade membrane surface receptor.

The present disclosure also relates to a tumor dissociation reagent which further does not comprise trypsin and collagenase and comprises hyaluronidase, wherein the tumor dissociation reagent does not degrade or partially degrade membrane surface receptor.

Wherein, the concentration range of the hyaluronidase described in an embodiment of the present disclosure is preferably 1 mg/mL or less, and the concentration of hyaluronidase is more preferably 1 µg/mL to 1 mg/mL.

The present disclosure further relates to the preceding tumor dissociation reagent, further comprising DNase I.

Wherein, the concentration range of the DNase I described in the present disclosure is preferably 50 µg/mL or less, and the concentration of DNase I is more preferably 1 µg/mL to 50 µg/mL.

In one embodiment, the tumor dissociation reagent does not degrade or partially degrade membrane surface receptor, wherein said membrane surface receptor is at least one checkpoint receptor selected from the group consisting of receptor CD8, PD-1, PD-L1, TIM-3 and LAG-3 protein.

In one embodiment, the proceeding membrane surface receptor is a checkpoint receptor.

In a further aspect, the present disclosure provides use of said tumor dissociation reagent in detecting protein expression level of an immunological checkpoint marker in tumor tissue.

In one embodiment of the present disclosure, the preceding tumor dissociation reagent further comprises DNase I.

In one embodiment of the present disclosure, the tumor tissue includes tumor infiltrating immune cell.

In an embodiment of the present disclosure, the protein expression in tumor tissue is detected by flow cytometry.

In an embodiment of the present disclosure, the protein is membrane surface receptor for checkpoint.

In an embodiment of the present disclosure, in flow cytometry of tumor tissue, said membrane surface receptor is at least one checkpoint receptor selected from the group consisting of CD8, PD-1, PD-L1, TIM-3 and LAG-3 protein.

In a further aspect, the present disclosure relates a kit for tumor dissociation comprising the tumor dissociation reagent of the present disclosure.

In an embodiment of the present disclosure, the preceding tumor dissociation reagent further comprises DNase I.

The present disclosure also relates to use of the kit in detecting protein expression in tumor tissue by flow cytometry.

In a further aspect, the present disclosure also provides a preparation method, wherein the method may prevent degradation of immunological checkpoint markers in tumor tissue, wherein cells are treated with the tumor dissociation agent disclosed by the present disclosure.

In one embodiment of the present disclosure, a method of tumor dissociation for flow cytometry comprises dissolving a tumor tissue with the tumor dissociation reagent of the present disclosure.

In one embodiment of the present disclosure, the tumor tissue further includes tumor infiltrating immune cell.

Advantageous Effects of the Invention

The benefit of the present disclosure resides in the establishment of a tumor dissociation reagent which does not comprise collagenase or trypsin and does not degrade or partially degrade membrane surface marker in tumor tissue, therefore the tumor dissociation reagent is useful in flow cytometry for detecting the expression level of proteins in tumor tissue.

DETAILED DESCRIPTION

Figure 1:
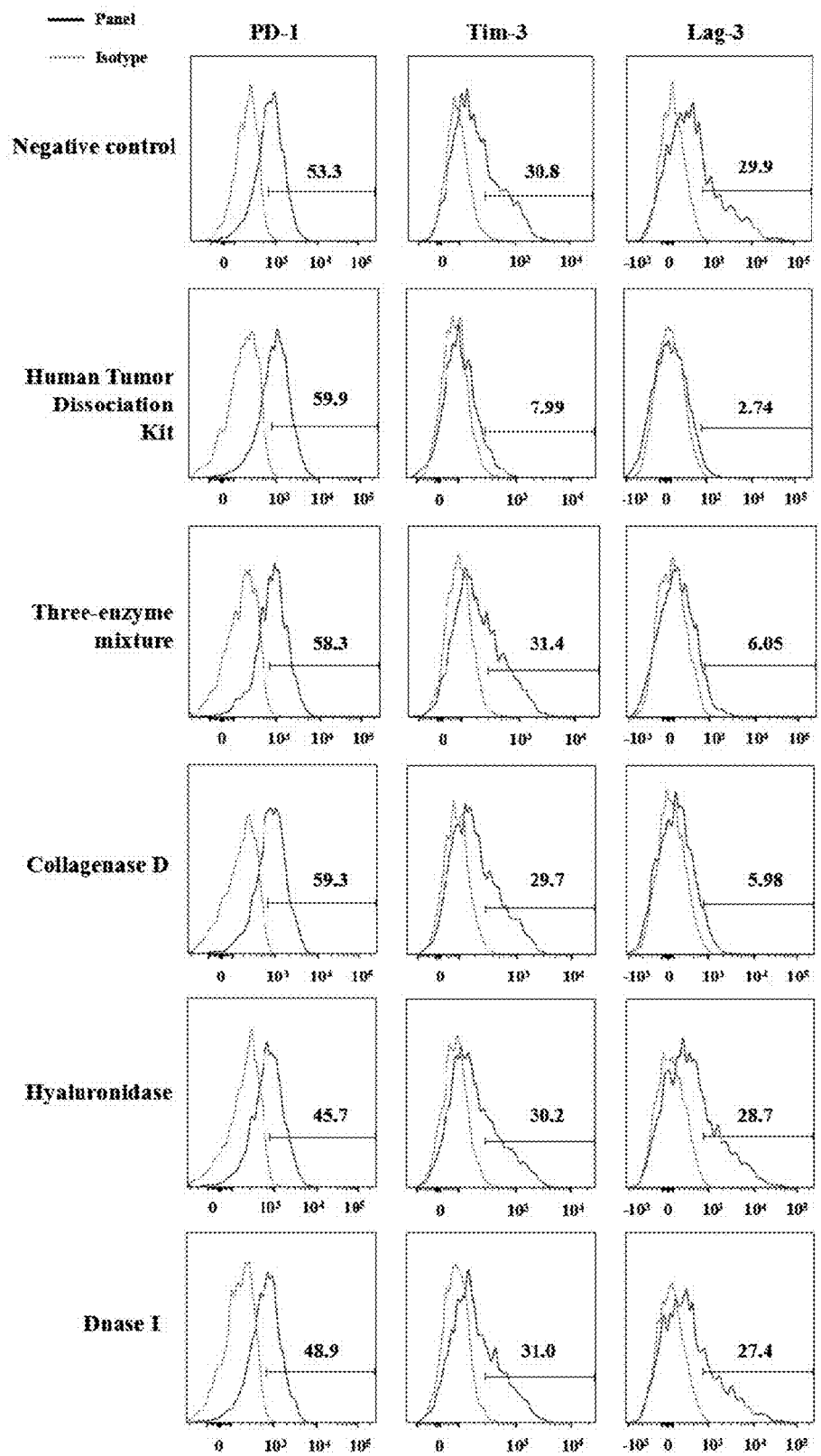
FIG. 1 is a flow chart showing the checkpoint proteins PD-1, Tim-3, and Lag-3 in helper T cells (CD4+) treated with different digestive enzymes.

The present disclosure is further described by the specific embodiments and experimental results. Although specific terms are used hereinafter for the purpose of clarity, these terms are not to be limiting the scope of the present disclosure.

As used herein, the term "dissociation reagent" refers to an enzymatic digestion reagent, and in the present disclosure, a tumor dissociation reagent refers to an enzymatic digestion reagent that digests tumor tissue into a single cell suspension with an enzyme digestion solution.

As used herein, the term "membrane surface receptor" refers to one molecule or a class of molecules on cell surface that may recognize, bind to a specific biologically active substance (referred to as a ligand), and the resulting complex may activate and initiate a series of physical and chemical changes that lead to the final biological effects of the substance. Changes in the various factors of the cell environment result in corresponding changes of the physiological processes within the cell through the role of the cell membrane receptors.

The experimental methods in the following examples, unless otherwise specified, are conventional methods.

EXAMPLES

Example 1

Preparation of Digestive Enzyme Reagents

Dissociation buffer system of Hyaluronidase: 50 μL of a solution of hyaluronidase with an initial concentration of 10 mg/mL (Hyaluronidase, available from Sigma, Cat. No. H3506) was added to 4.95 mL of DMEM medium (the final concentration of hyaluronidase is 100 μg/mL) and then formulated into 5 mL of dissociation reagent for tumor tissues.

Dissociation buffer system of Collagenase D: 500 μL of a solution of collagenase D (Collagenase D, available from Roche Corporation, Cat. No. 11088882001) with an initial concentration of 10 mg/mL was added to 4.5 mL of DMEM medium (the final concentration of collagenase D is 1 mg/mL) and then formulated into 5 mL of dissociation reagent for tumor tissues.

Dissociation buffer system of DNase I: 50 μL of a solution of DNase I (DNase I, available from Sigma Corporation, Cat. No. DN25-1G) with an initial concentration of 5 mg/mL was added to 4.95 mL of DMEM medium (the final concentration of DNase I is 0.05 mg/mL) and then formulated into 5 mL of dissociation reagent for tumor tissues.

Dissociation buffer system of three-enzyme mixture: 50 μL of a solution of hyaluronidase at the initial concentration of 10 mg/mL, 500 μL of a solution of collagenase D with an initial concentration of 10 mg/mL and 50 μL of a solution of DNase I with an initial concentration of 5 mg/mL were added to 4.4 mL of DMEM medium and then formulated into 5 mL of dissociation reagent for tumor tissues.

Dissociation buffer system of two-enzyme mixture: 50 μL of a solution of hyaluronidase with an initial concentration of 10 mg/mL and 50 μL of a solution of DNase I with an initial concentration of 5 mg/mL were added to 4.9 mL of DMEM medium and then formulated into 5 mL of dissociation reagent for tumor tissues.

Dissociation buffer system of Miltenyi Human Tumor Dissociation Kit (Human tumor dissociation kit, Cat. No. 130-095-929): according to the instructions, the storage solution of digestive enzymes A, H, and R with appropriate concentrations are formulated, and then stored at −20° C. In the experiment, 200 μL of storage solution of enzyme H, 100 μL of storage solution of enzyme R and 25 μL of storage solution of enzyme A were added to 4.7 mL of DMEM medium and then formulated into 5 mL of dissociation solution for tumor tissues.

Example 2

Design of Flow Staining

Specific designs of different staining channels on cell surface are shown in Table 1.

TABLE 1

Channels used for cell surface molecular markers

| Channel | Blank | Isotype 2 | Panel 2 |
|---|---|---|---|
| FITC | — | Isotype | Tim3 |
| PE | — | Isotype | PD-1 |
| PerCP | — | CD4 | CD4 |
| PE-Cy7 | — | Isotype | Lag-3 |
| APC | — | CD3 | CD3 |
| APC-Cy7 | — | CD8 | CD8 |
| BV421 | Live/Dead | Live/Dead | Live/Dead |
| BV510 | — | CD45 | CD45 |

Example 3

Effects of Different Digestive Enzymes on the Positive Rate of Checkpoint Proteins PD-1, TIM3 and LAG-3

The expression of PD-1, Tim-3 and Lag-3 in cytoxic T cells (CD8+T) and helper T cells (CD4+T) was induced by PHA treatment. Whether or not different digestive enzymes will affect expression levels of the three proteins was analyzed in these two groups of cells.

The tumor is not a single cell suspension, thus it cannot be used in flow cytometry directly. If mechanical dissociation is used rather than enzymatic dissociation, single-cell yield is relatively low, therefore positive rate of single cell molecular marker proteins obtained by mechanical dissociation may not be able to represent the real value of the whole tissue. Thus, in the present disclosure, peripheral blood mononuclear cells were used in the detection of molecular marker proteins of cells. It is confirmed that some dissociation reagent has an effect on the expression level of marker proteins on cell surface.

First, cryopreserved human peripheral blood mononuclear cells (PBMC) were revived and then treated with 10 μg/mL of PHA for 48 hours to allow the cells to be activated, followed by counting. The cells were aliquoted into 21 tubes; the number of cells is $3 \times 10^5$ cells per tube. 5 mL of dissociation buffer was added into each tube, while 5 mL of DMEM medium (available from Gibco, Cat. No. 11960-051) was added into negative control tube. The tubes were put into a 37° C. water bath (available from Shanghai Yiyou Company, model THZ-82), and the cells were digested for 15 minutes. The specific information of different treatment groups are as followed:

TABLE 2

Dissociation conditions in different treatment groups

| Name | Dissociation Reagent | Condition |
|---|---|---|
| PBMC | Negative control | 37° C., 15 minutes |
|  | Miltenyi Human Tumor Dissociation Kit (Kit) | 37° C., 15 minutes |
|  | Three-enzyme mixture | 37° C., 15 minutes |
|  | 1 mg/mL Collagenase D | 37° C., 15 minutes |
|  | 100 μg/mL Hyaluronidase | 37° C., 15 minutes |
|  | 0.05 mg/mL DNase I | 37° C., 15 minutes |
|  | Two-enzyme mixture | 37° C., 15 minutes |

The dissociated cells were centrifuged with a centrifuge (available from Eppendorf, model 5810R) and the supernatant was removed. The pellets were washed twice with a phosphate buffer PBS (available from Hyclone Corporation, Cat. No. SH3002802B) and centrifuged to remove the supernatant, and then incubated with formulated antibody mixture at 4° C. for 30 minutes in dark.

The cells were centrifuged at 4° C., 300×g to remove the supernatant. The cells were resuspended in 200 μL of staining buffer for flow cytometry (available from BD Co., Cat. No. Pharmingen-554657) and centrifuged at 4° C., 300×g for 5 minutes, and repeated once.

The cells were re-suspended in 100 μL of cell fixation buffer (available from BD, Cat. No. BD-554655) and incubated at 4° C. for 20-30 minutes in dark.

The cells were re-suspended in 200 μL of staining solution (available from BD Co., Cat. No. Pharmingen-554657), centrifuged at 4° C., 300×g for 5 minutes and repeated once, and finally re-suspended in staining buffer for flow cytometry (available from BD Company, Cat. No. Pharmingen-554657), and the suspension was transferred to a flow tube with a final volume of 500 μL and detected with a cytometer (BD FACS Canto II).

The expression levels of Tim-3 and Lag-3 proteins in T cells (CD4+) and cytoxic T cells (CD8+) were significantly decreased after treatment with Miltenyi Human Tumor Dissociation Kit for 15 minutes as compared with the negative control. Similarly, the expression levels of Lag-3 protein in helper T cells (CD4+) and cytoxic T cells (CD8+) were significantly decreased after treatment with three-enzyme mixtures or collagenase (as shown in FIG. 1, FIG. 2, FIG. 3 and TABLE 3).

Figure 2:
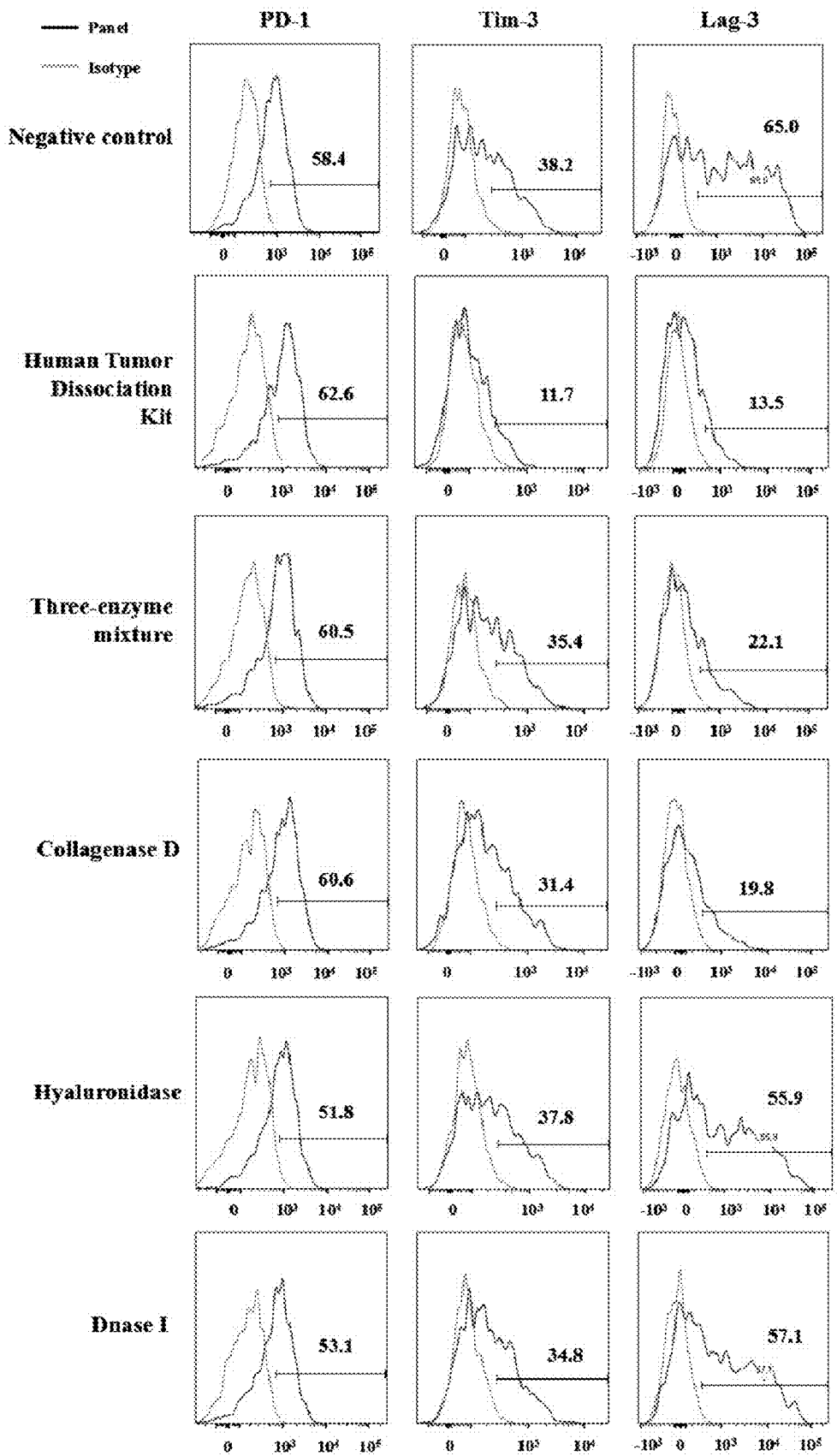
FIG. 2 is a flow chart showing the checkpoint proteins PD-1, Tim-3, and Lag-3 in cytoxic T cells (CD8+) treated with different digestive enzymes.
Figure 3:
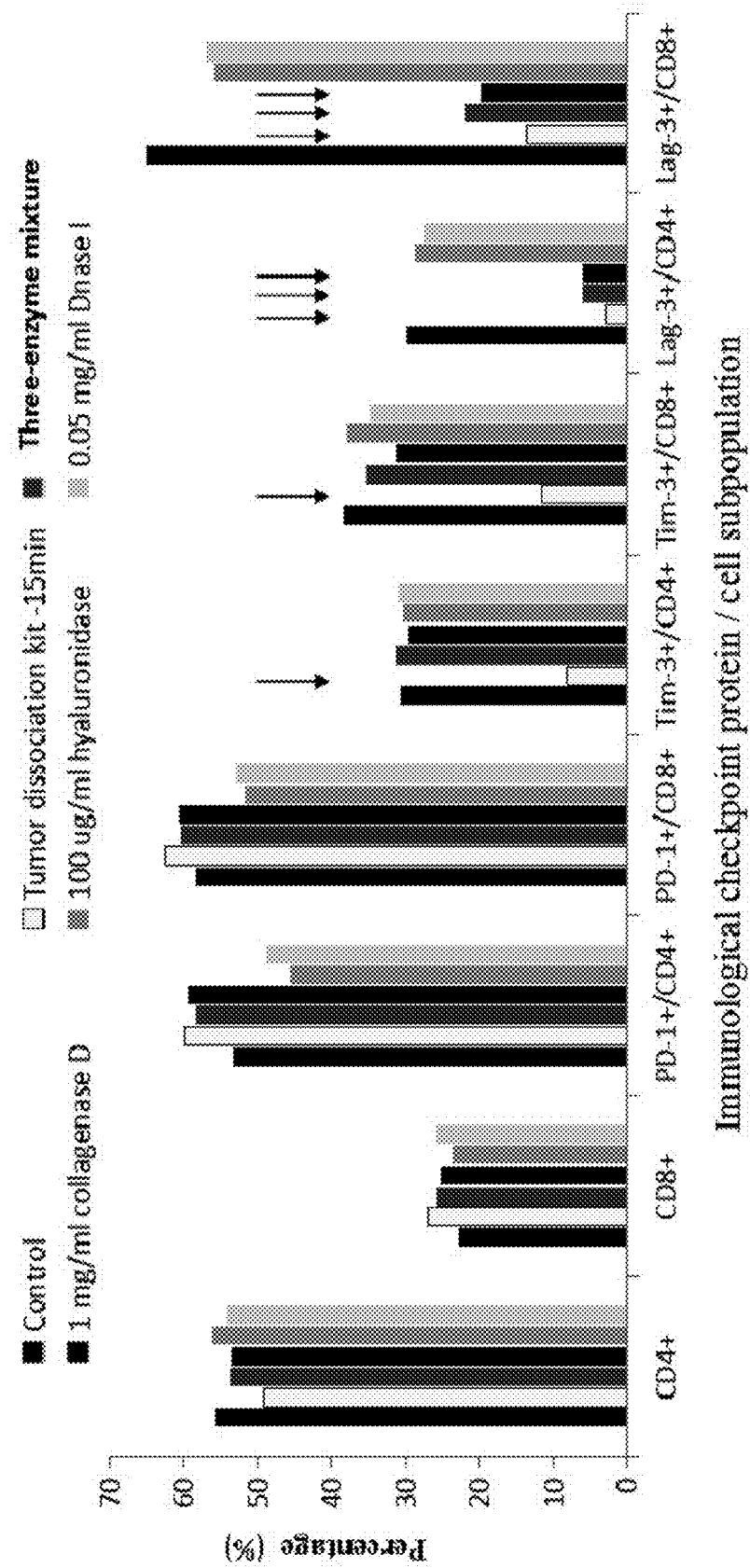
FIG. 3 is a graph showing the percentages of cell surface checkpoint proteins after different digestive enzymes treatment.

In contrast, the expression of different cell surface molecular markers such as PD-1, Tim-3, and Lag-3 in the hyaluronidase or DNase I treatment group was unchanged or not significantly decreased as compared with the negative control group (as shown in FIG. 1, FIG. 2, FIG. 3 and TABLE 3). This suggests that the treatment of collagenase or Miltenyi Human Tumor Dissociation Kit will affect the expression levels of one or more molecular markers on cell surface such as Tim-3 and Lag-3, which is disadvantageous for further detection in flow cytometry. But the reagents not containing collagenase, such as hyaluronidase or DNase I alone did not affect the expression of these immune cell surface molecular markers under given conditions. This experiment demonstrated that neither DNase I at given dose nor hyaluronidase affected the expression level of the checkpoint proteins. Furthermore, we found that the results of 1 mg/mL hyaluronidase or 1 μg/mL hyaluronidase treatment were consistent with that of 100 μg/mL hyaluronidase treatment that neither one affected the level of cell surface molecular markers such as CD8, PD-1, Tim-3 and Lag-3. Similarly, the expression of PD-1, Tim-3 and Lag-3 were not reduced after treatment with up to 50 μg/mL of DNase I.

Although the fluorescence signal of CD8 was significantly reduced and PD-1 positive rate was slightly increased, the fluorescence signal intensities of other immunological checkpoints were not decreased. And treatment with less than 50 μg/mL of DNase I did not affect the detection of molecular markers.

Figure 4:
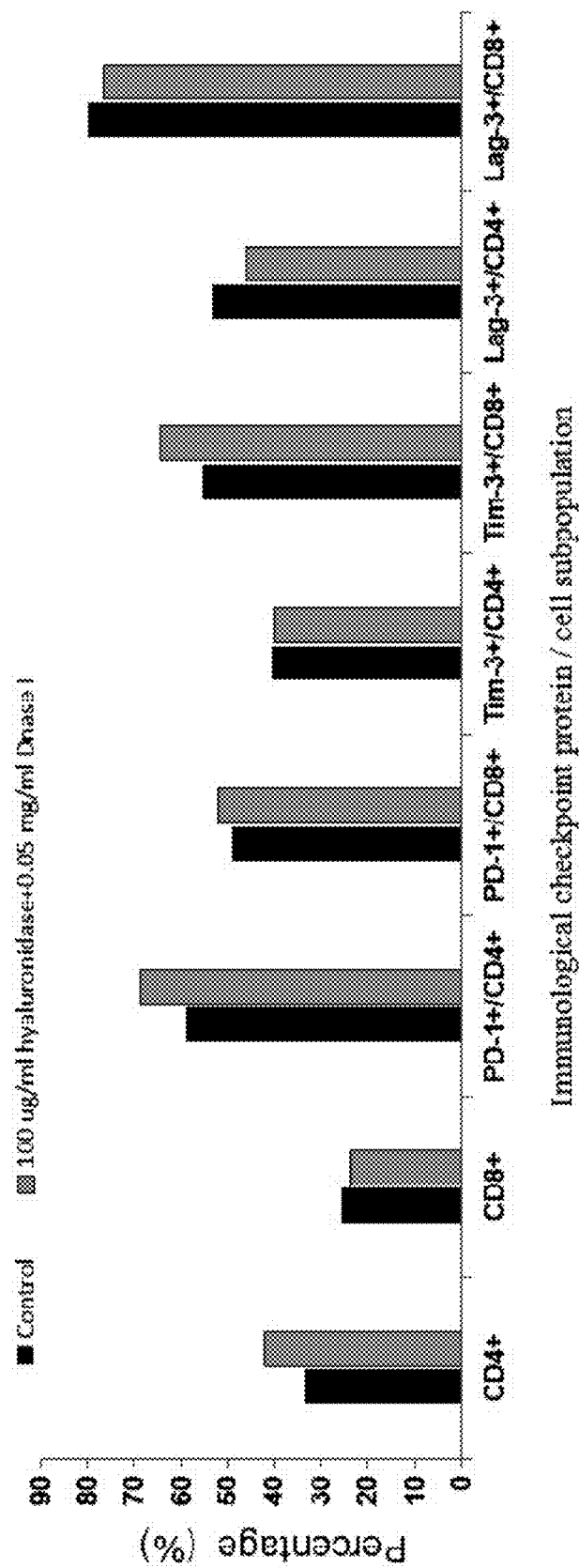
FIG. 4 is a graph showing the percentages of cell surface checkpoint proteins PD-1, Tim-3 and Lag-3 after treatment with two-enzyme mixture.

To further verify the protective effect of the hyaluronidase group or DNase I on the cell surface molecular markers, a mixture of DNase I and hyaluronidase was used to treat human peripheral blood mononuclear cells (PBMC) according to above experimental method. The experimental results indicated that the mixture of DNase I and hyaluronidase did not affect the expression level of the checkpoint proteins (as shown in FIG. 4 and Table 4). This data was also advantageous in the increased selectivity for enzyme species. It is anticipated that in certain tumor samples, the cell yield can be increased while the protein expression level is altered.

TABLE 3

Positive expression rates (%) of different cell surface molecular markers

| Group | CD4+ | CD8+ | PD-1+/CD4+ | PD-1+/CD8+ | Tim-3+/CD4+ | Tim-3+/CD8+ | Lag-3+/CD4+ | Lag-3+/CD8+ |
|---|---|---|---|---|---|---|---|---|
| Negative control | 55.80 | 22.80 | 53.30 | 58.40 | 30.80 | 38.20 | 29.90 | 65.00 |
| Kit | 49.10 | 27.10 | 59.90 | 62.60 | 7.99 | 11.70 | 2.74 | 13.50 |
| Three-enzyme mixture | 53.70 | 25.80 | 58.30 | 60.50 | 31.40 | 35.40 | 6.05 | 22.10 |
| Collagenase D | 53.50 | 25.20 | 59.30 | 60.60 | 29.70 | 31.40 | 5.98 | 19.80 |
| Hyaluronidase | 56.10 | 23.60 | 45.70 | 51.80 | 30.20 | 37.80 | 28.70 | 55.90 |
| DNase I | 54.10 | 25.90 | 48.90 | 53.10 | 31.00 | 34.80 | 27.40 | 57.10 |

TABLE 4

Positive expression rate (%) of different cell surface molecular markers after treatment with the two-enzyme mixture

| Group | CD4+ | CD8+ | PD-1+/CD4+ | PD-1+/CD8+ | Tim-3+/CD4+ | Tim-3+/CD8+ | Lag-3+/CD4+ | Lag-3+/CD8+ |
|---|---|---|---|---|---|---|---|---|
| Negative control | 33.7 | 25.9 | 59 | 49.4 | 40.6 | 55.2 | 53.2 | 79.9 |
| Two-enzyme mixture | 42.2 | 24 | 68.7 | 52.2 | 39.9 | 64.5 | 46.1 | 76.5 |

Example 4

Detection of Surface Marker CD8 on Human Peripheral Blood Mononuclear Cells (PBMC)

Cryopreserved human peripheral blood mononuclear cells (PBMC) were revived and then treated with 10 μg/mL of PHA for 48 hours to allow the cells to be activated, followed by counting. The cells were aliquoted, the number of cells is $3 \times 10^5$ cells per tube. 5 mL of dissociation buffer was added into each tube, while 5 mL of DMEM medium (available from Gibco, Cat. No. 11960-051) was added into negative control tube. The tubes were put into a 37° C. water bath (available from Shanghai Yiyou Company, model THZ-82), and the cells were digested for 60 minutes.

Figure 5:
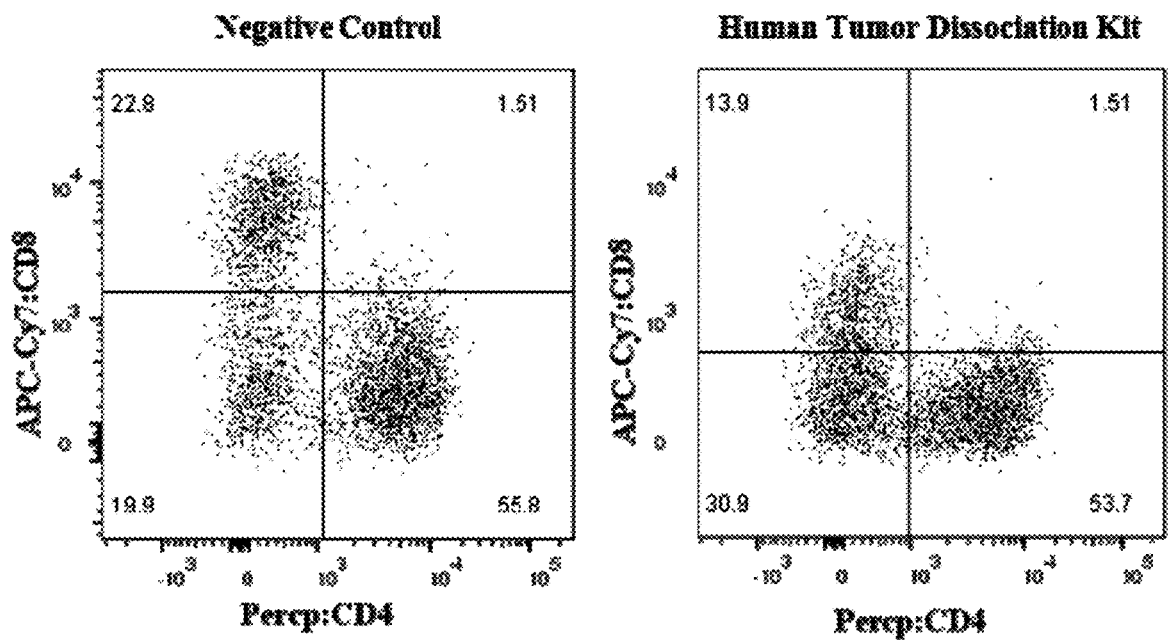
FIG. 5 is a flow chart showing the cell surface checkpoint proteins CD4 and CD8 after treatment with different digestive enzymes.

The other steps were the same as that in Example 3, and it was found that the fluorescence intensity of CD8 was decreased after the treatment with the commercial human tumor kit (Accumax Cell Dissociation Solution) for 60 minutes, indicating that the kit treatment reduced the expression level of CD8 (as shown in FIG. 5 and Table 5).

TABLE 5

Positive expression rates (%) of cell surface molecular markers CD4 and CD8 after treatment with Kit

| Group | CD4+ | CD8+ |
|---|---|---|
| Negative control | 55.80 | 22.80 |
| Kit; 60 minutes | 53.70 | 13.90 |

Example 5

Treatment of Human Tumor Tissues

Clinical samples obtained by operation were placed in prepared MACS tissue preservation solution and transported to WuXi AppTec Co. Ltd. (Shanghai). at 4° C. These tumor samples were treated within 48 hours after surgery. Before treatment of clinical tumor tissues, numbering of the corresponding sample was carried out, and the medical history of the patient, texture and color of the tumor tissues, and clinical information were recorded. Tumor tissues were weighed.

First, the obvious adipose tissue, fibrous tissue and necrotic part were removed, and then the resulting clinical tumor samples were washed three times in pre-cooled DMEM medium, finally the tumor tissue were cut into 10 mm³ small pieces with ophthalmic scissors and tweezers.

50 μL of a solution of hyaluronidase with an initial concentration of 10 mg/mL was added to 4.95 mL of DMEM medium (the final concentration is 100 μs/mL) to prepare the dissociation reagent for tumor tissue, and then 5 mL of prepared dissociation reagent for tumor tissue was put into a C tube dedicated for gentleMACS Dissociator (available from Miltenyi Company, Cat. No. 130-093-237), and the cut tumor tissues were also transferred to the C tube dedicated for Miltenyi tissue treatment with tweezers. After tightening of the lid, the tissue fragments in the dissociation reagent were gently shaken. Tumor tissues within the range of 10 mg to 1000 mg can be treated with this dissociation system.

The C tube was gently inserted into the C-tube slot of the gentleMACS Dissociator (available from Miltenyi Company, Cat. No. 130-093-235). And it should be noted that the tumor tissue fragments should be concentrated at the blade area within the C tube.

The program was set to the h_tumor_01, and then run once. The C tube was removed after the end of the program h_tumor_01 and placed upward for a while so as to place all tumor fragments in the dissociation solution at the bottom of the tube. If necessary, the lid can be removed and the tissue adhered on the lid can be transferred with tweezers to the bottom dissociation reagent. The removed C tube was put into a 37° C. constant temperature water bath for 7 minutes, which can be shook appropriately for several times during the period. Repeat the above steps once.

The above C tube was gently inserted into the C-tube slot of the Miltenyi Tissue processor. The program was set to h_tumor_02, and then run twice. The C tube was removed and the tissue dissociation was re-suspended in 20 mL of phosphate buffer. A 70 μm cell strainer (available from falcon, Cat. No. 352350) was placed on a 50 mL centrifuge tube and the dissociated tissue was re-suspended and slowly passed through the 70 μm cell strainer and, if necessary, the minced fine tissue pieces can be grounded on the strainer to obtain more single-cell suspensions. The cell strainer was washed with 20 mL to 30 mL of phosphate buffer so that the final volume of the single-cell suspension obtained through the strainers was 50 mL.

The cells were centrifuged at 300×g for 10 minutes, and the supernatant was removed with a pipette.

The single cells obtained in the previous step were re-suspended in 40 mL of phosphate buffer and were centrifuged at 300×g for 7 min.

The cells were re-suspended into a single-cell suspension with 0.5 to 5 mL of flow cytometry staining buffer, and counted by staining of trypan blue.

Example 6

Comparison of Cell Digestion Rates in Different Enzyme-Treated Groups

The clinically obtained patient tumor samples were dissociated with different digestive enzymes under the same temperature and time conditions according to the method of Example 5, and the single-cell yield was counted with trypan blue staining. Each sample was counted three times, and the average number+SEM of single cells per gram of tumor was shown in the figure.

Figure 6:
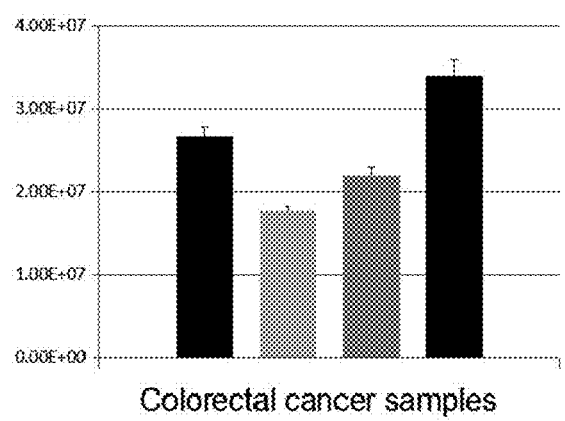
FIG. 6 is a graph showing the cell yield after digestion with different enzymes.
Figure 6:
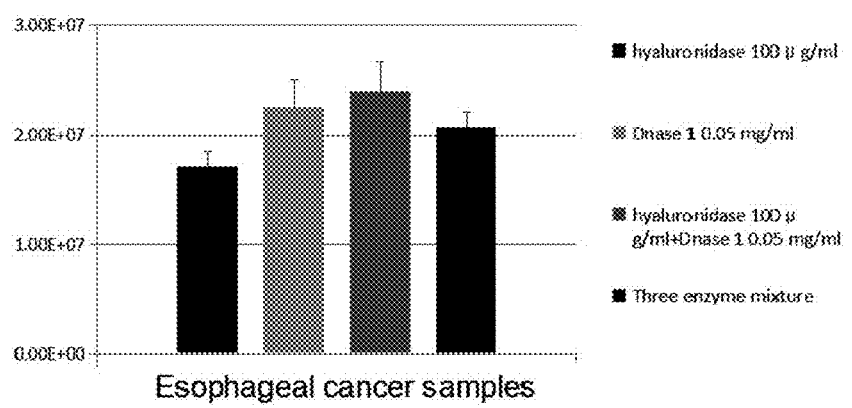

In FIG. 6, although the cell yield varies depending on the tumor species or states between different samples, it is comparable between the combination of the three enzymes involved in the present disclosure and the conventional enzyme combination methods reported in the literature, and the differences of cell yield were not large, thus the resulting cells were sufficient for further flow cytometry analysis.

Although the present disclosure is not limited thereto, it will be understood by those skilled in the art that various modifications and variations can be made within the scope of the present disclosure, the manner of changes are also within the scope of the present disclosure.

The invention claimed is:

1. A method of detecting expression of a membrane surface receptor in a tumor tissue by flow cytometry, comprising
  dissociating a tumor tissue with a tumor dissociation reagent, wherein the tumor dissociation reagent does not comprise collagenase but comprises a hyaluronidase having a concentration of 100 μg/ml and a DNase I having a concentration of 50 μg/ml;
  wherein the tumor dissociation reagent does not degrade or does not partially degrade membrane surface receptor; and
  detecting expression of the membrane surface receptor in the tumor tissue by flow cytometry,
  wherein the membrane surface receptor is selected from the group consisting of CD8, PD-I, PD-LI, TIM-3 and LAG-3 protein,
  and wherein cells from the dissociated tumor tissue are centrifuged, washed, and suspended in flow cytometry buffer before detecting.

2. The method according to claim 1, wherein the tumor dissociation reagent does not comprise trypsin.

3. The method according to claim 1, wherein the tumor tissue includes tumor infiltrating immune cell.

\* \* \* \* \*